(12) United States Patent
Dube

(10) Patent No.: US 9,198,567 B1
(45) Date of Patent: Dec. 1, 2015

(54) LARYNGOSCOPE WITH PRESSURE SENSITIVE BLADE

(71) Applicant: Nkosiyalinda Dube, Rockwall, TX (US)

(72) Inventor: Nkosiyalinda Dube, Rockwall, TX (US)

( * ) Notice: Subject to any disclaimer, the term of this patent is extended or adjusted under 35 U.S.C. 154(b) by 346 days.

(21) Appl. No.: 13/916,018

(22) Filed: Jun. 12, 2013

(51) Int. Cl.
*A61B 1/267* (2006.01)

(52) U.S. Cl.
CPC ...................................... *A61B 1/267* (2013.01)

(58) Field of Classification Search
CPC ......................................................... A61B 1/267
USPC ...................... 328/128; 128/200.26; 600/200
See application file for complete search history.

(56) References Cited

U.S. PATENT DOCUMENTS

| 3,888,117 | A | 6/1975 | Lewis |
| 4,295,465 | A | 10/1981 | Racz et al. |
| 5,536,245 | A | 7/1996 | Dahlbeck |
| 2004/0122292 | A1 * | 6/2004 | Dey et al. ...................... 600/190 |

* cited by examiner

*Primary Examiner* — Christopher Beccia
*Assistant Examiner* — Diana S Jones
(74) *Attorney, Agent, or Firm* — Crossley Patent Law

(57) ABSTRACT

A laryngoscope with pressure sensitive blade including a removable polymeric section disposed for engagement against a patient's maxillary incisors during intubation, said polymeric section including a rubberlike upper surface for placement against said patient's teeth, and an undersurface disposed in contact with the laryngoscope, wherein a pressure sensor disposed upon the polymeric section undersurface signals pressure exerted atop the upper surface by means of an illuminable signal, said illuminable signal emitting a first color when pressure is sensed atop the polymeric section, and alternately a second color when said pressure is sensed exceeding a pressure threshold.

2 Claims, 3 Drawing Sheets

LARYNGOSCOPE WITH PRESSURE SENSITIVE BLADE

BACKGROUND OF THE INVENTION

Various types of laryngoscopes are known in the prior art. However, what is needed is a laryngoscope with pressure sensitive blade that includes a removable polymeric section disposed for engagement against a patient's maxillary incisors during intubation, said polymeric section including a rubberlike upper surface for placement against said patient's teeth, and an undersurface disposed in contact with the laryngoscope, wherein a pressure sensor disposed upon the polymeric section undersurface signals pressure exerted atop the upper surface by means of an illuminable signal, said illuminable signal emitting a first color when pressure is sensed atop the polymeric section, and alternately a second color when said pressure is sensed exceeding a pressure threshold.

FIELD OF THE INVENTION

The present invention relates to a laryngoscope with pressure sensitive blade, and more particularly, to a laryngoscope with pressure sensitive blade that includes a removable polymeric section disposed for engagement against a patient's maxillary incisors during intubation, said polymeric section including a rubberlike upper surface for placement against said patient's teeth, and an undersurface disposed in contact with the laryngoscope, wherein a pressure sensor disposed upon the polymeric section undersurface signals pressure exerted atop the upper surface by means of an illuminable signal, said illuminable signal emitting a first color when pressure is sensed atop the polymeric section, and alternately a second color when said pressure is sensed exceeding a pressure threshold.

SUMMARY OF THE INVENTION

The general purpose of the laryngoscope with pressure sensitive blade, described subsequently in greater detail, is to provide a laryngoscope with pressure sensitive blade which has many novel features that result in a laryngoscope with pressure sensitive blade which is not anticipated, rendered obvious, suggested, or even implied by prior art, either alone or in combination thereof.

It is quite easy, and fairly common, to render damage to a patient's teeth during intubation when applying a laryngoscope to the oral cavity. Force against the maxillary incisors as the laryngoscope is applied to the throat can cause discomfort and pain—especially when administered by an inexperienced medical practitioner.

What is needed is a laryngoscope that includes a polymeric section disposed to engage against a patient's maxillary incisors to prevent damage thereto, and a pressure sensor able to signal pressure applied to the teeth exceeding a particular pressure threshold.

The present laryngoscope with pressure sensitive blade, therefore, includes a polymeric section removably disposed atop the laryngoscope in a position suitable for engagement against a patient's maxillary incisors during use. The polymeric section includes a rubberlike upper surface for engagement against the patient's maxillary incisors and an undersurface that rests atop the laryngoscope when the polymeric section is installed therein.

A pressure sensor is disposed upon the undersurface and engaged against the laryngoscope when the polymeric section is installed to the laryngoscope. Pressure exerted atop the upper surface of the polymeric section is thus sensed by the pressure sensor during use.

The pressure sensor is disposed in operational communication with an illuminable signal emitted from the polymeric section, whereby pressure sensed atop the polymeric section illuminates a first color when pressure is sensed there atop, and alternately a second color when pressure increases above a particular pressure threshold. Thus, over-forcing by a medical practitioner wielding the device is signaled immediately by the illumination of the second color, whereby preventative action may be taken.

In the preferred embodiment herein disclosed the first color is contemplated to be white and the second color red. The illuminable signal is disposed upon the polymeric section to remain visible during use of the device. The illuminable signal may be effected by a Light Emitting Diode.

To provide means to power the pressure sensor and illuminable signal, a battery compartment is disposed interior to the polymeric section. The battery compartment is accessible through the undersurface of the polymeric section when said polymeric section is removed from the laryngoscope and a battery stored therein is therefore changeable, when needed, after repeated use of the laryngoscope.

Thus has been broadly outlined the more important features of the present laryngoscope with pressure sensitive blade so that the detailed description thereof that follows may be better understood and in order that the present contribution to the art may be better appreciated.

Objects of the present laryngoscope with pressure sensitive blade, along with various novel features that characterize the invention are particularly pointed out in the claims forming a part of this disclosure. For better understanding of the laryngoscope with pressure sensitive blade, its operating advantages and specific objects attained by its uses, refer to the accompanying drawings and description.

BRIEF DESCRIPTION OF THE DRAWINGS

Figures

DETAILED DESCRIPTION OF THE DRAWINGS

Figure 1:
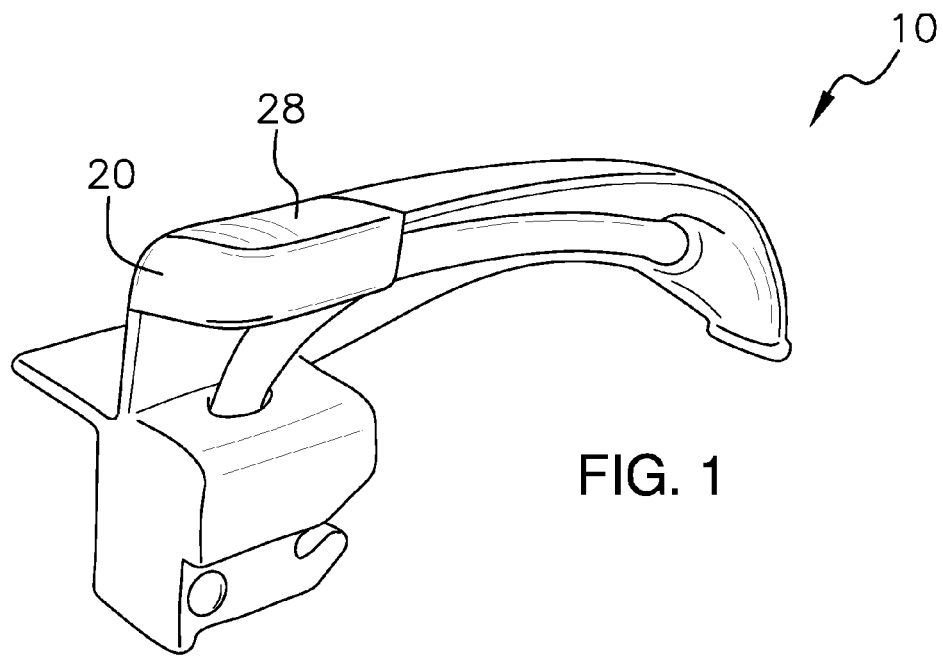
FIG. 1 is an isometric view.
Figure 2:
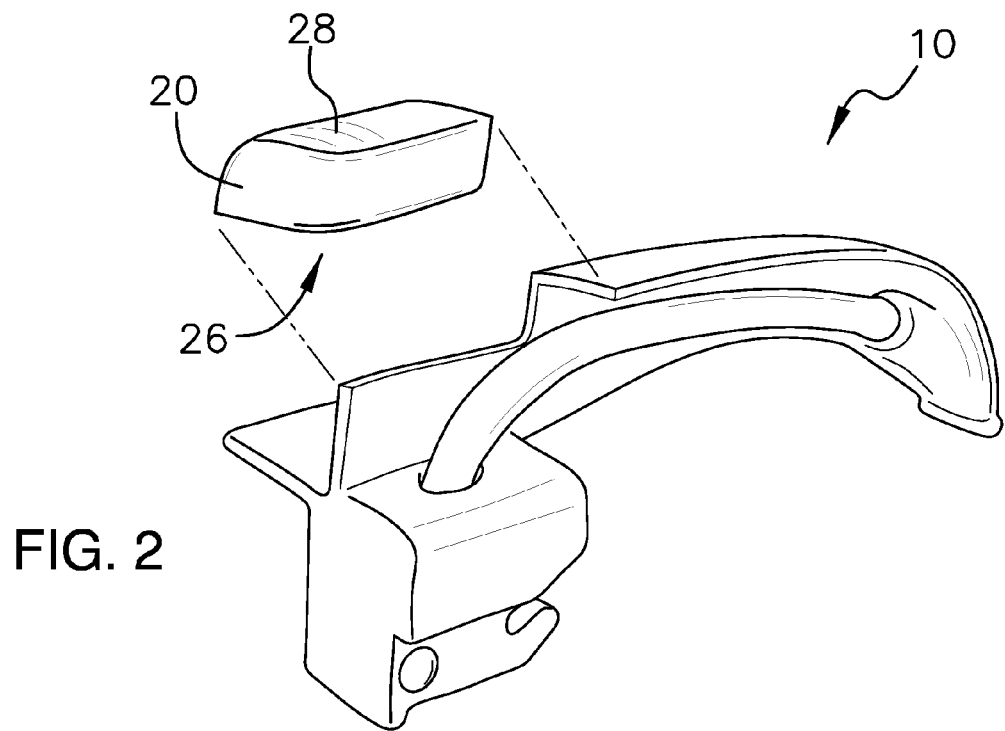
FIG. 2 is an exploded view.
Figure 3:
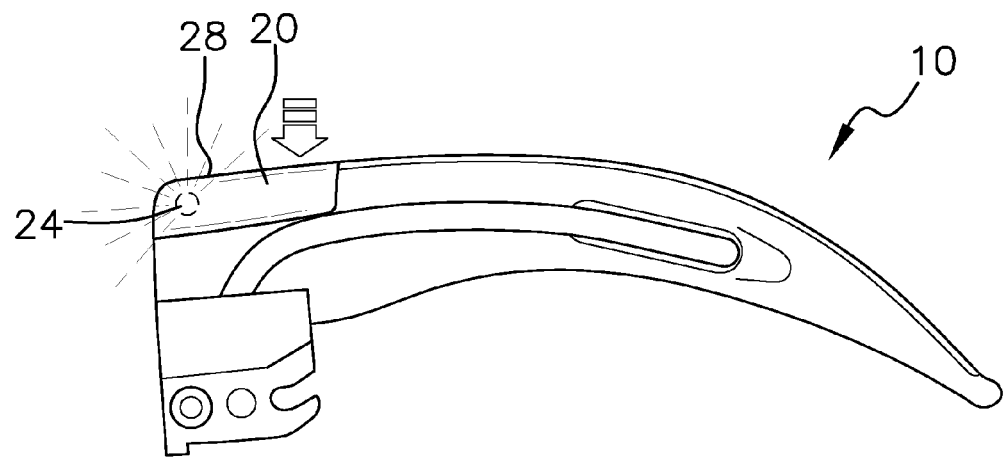
FIG. 3 is a side view.
Figure 4:
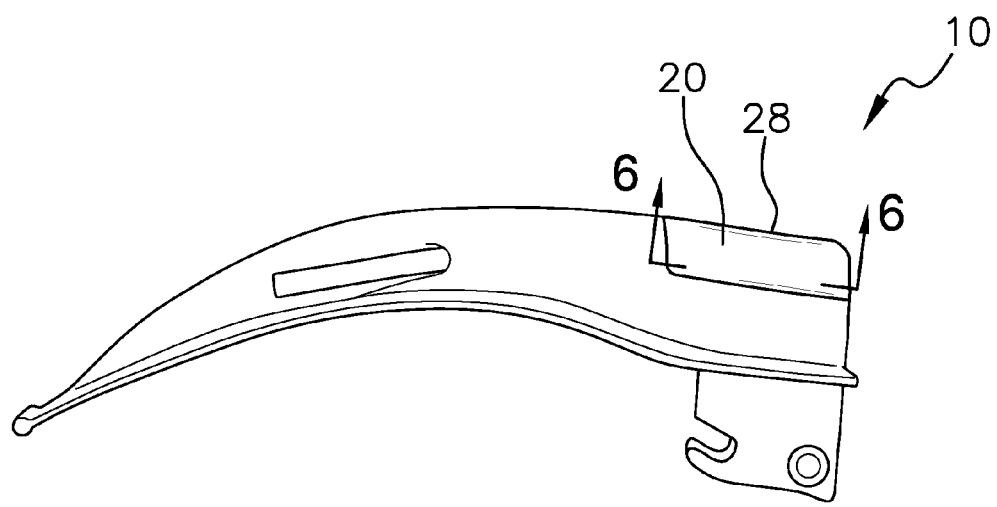
FIG. 4 is a side view.
Figure 5:
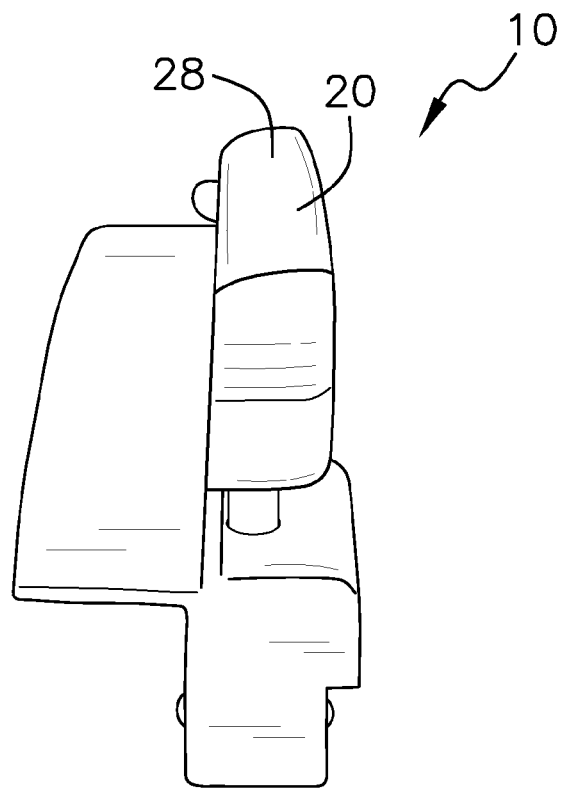
FIG. 5 is a back view.
Figure 6:
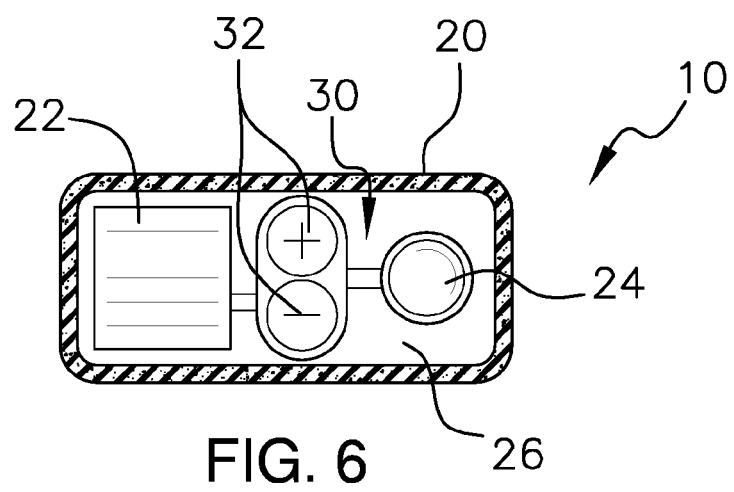
FIG. 6 is a cross-section view taken along the line 6-6 of FIG. 4.

With reference now to the drawings, and in particular FIGS. 1 through 6 thereof, example of the instant laryngoscope with pressure sensitive blade employing the principles and concepts of the present laryngoscope with pressure sensitive blade and generally designated by the reference number 10 will be described.

Referring to FIGS. 1 through 6 a preferred embodiment of the present laryngoscope with pressure sensitive blade 10 is illustrated.

The present laryngoscope with pressure sensitive blade 10 has been devised to increase patient comfort during intubation through the oral cavity. The present laryngoscope with pressure sensitive blade 10 includes a polymeric section 20 disposed to engage against a patient's maxillary incisors during use, whereby said patient's teeth are protected from damage when engaged against said polymeric section 20.

To prevent over-forcing by a medical practitioner when conducting the intubation procedure, a pressure sensor 22 is disposed within the polymeric section 20, said pressure sensor 22 in operational communication with an illuminable signal 24 emitted from the polymeric section 20 when pressure is sensed atop the polymeric section 20. The illuminable signal 24 is contemplated to illuminate a first color when pressure at the polymeric section 20 is sensed beneath a particular pressure threshold, thence illuminate a second color when the pressure sensed at the polymeric section 20 is in excess of said pressure threshold.

The laryngoscope with pressure sensitive blade 10, therefore, includes a removable polymeric section 20 for engaging against a patient's maxillary incisors during use. The polymeric section 20 includes an undersurface 26 disposed in contact with the laryngoscope when installed thereat, and an upper surface 28 disposed to contact a patient's teeth during use. The upper surface 28 is contemplated to be soft, rubber-like, and durable for engagement against a patient's maxillary incisors without rendering damage thereto. The rubberlike texture afforded the polymeric section 20 upper surface 28 further prevents slippage of the teeth there against.

A pressure sensor 22 is disposed upon the undersurface 26 of the polymeric section 20 and is engaged against the laryngoscope when the polymeric section 20 is installed to said laryngoscope, whereby pressure atop the upper surface 28 is readable.

An illuminable signal 24 is emitted during use, said illuminable signal 24 responsive to pressure sensed by the pressure sensor 22. The illuminable signal 24 is contemplated to illuminate a first color when the pressure sensed 22 at the undersurface 26 of the polymeric section 20 is beneath a particular pressure threshold and to illuminate a second color when said pressure is sensed above said pressure threshold. In the preferred embodiment herein disclosed, the first color is contemplated to be white and the second color, red.

To provide means for powering the illuminable signal 24 and the pressure sensor 22, a battery compartment 30 is disposed upon the polymeric section 20. The battery compartment 30 is accessible through the undersurface 26 of the polymeric section 20 whereby a battery 32 may be changed, as needed, after repeated use.

What is claimed is:

1. A laryngoscope with pressure sensitive blade comprising:
   a polymeric section for engaging against a patient's maxillary incisors during use;
   a pressure sensor disposed upon the polymeric section; and
   an illuminable signal responsive to pressure sensed by the pressure sensor;
   wherein the illuminable signal illuminates a first color when the pressure sensed underneath the polymeric section is beneath a pressure threshold and the illuminable signal illuminates a second color when said pressure is sensed above the pressure threshold;
   wherein the polymeric section is removable from the laryngoscope with pressure sensitive blade; and
   wherein the polymeric section encloses a battery compartment to power the pressure sensor and the illuminable signal, said battery compartment accessible from an undersurface of the polymeric section.

2. A laryngoscope with pressure sensitive blade comprising:
   a removable polymeric section for engaging against a patient's maxillary incisors during use, said polymeric section comprising an undersurface disposed in contact with the laryngoscope, when installed, and an upper surface disposed to contact a patient's teeth when in use;
   a pressure sensor disposed upon the undersurface of the polymeric section;
   an illuminable signal responsive to pressure sensed by the pressure sensor; and
   a battery compartment disposed upon the polymeric section, said battery compartment accessible through the undersurface of the polymeric section;
   wherein the illuminable signal illuminates a first color when the pressure sensed underneath the polymeric section is beneath a pressure threshold and the illuminable signal illuminates a second color when said pressure is sensed above the pressure threshold.

* * * * *